United States Patent
Cross et al.

(10) Patent No.: US 10,004,248 B2
(45) Date of Patent: Jun. 26, 2018

(54) PACKAGE RECOGNITION SYSTEM

(71) Applicant: Conopco, Inc., Englewood Cliffs, NJ (US)

(72) Inventors: David Murray Cross, Letchworth (GB); Michael Paton, Royston (GB); Daniel Thomas Toon, Epping (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 454 days.

(21) Appl. No.: 14/408,617

(22) PCT Filed: Jul. 2, 2013

(86) PCT No.: PCT/EP2013/063942
§ 371 (c)(1),
(2) Date: Dec. 17, 2014

(87) PCT Pub. No.: WO2014/006048
PCT Pub. Date: Jan. 9, 2014

(65) Prior Publication Data
US 2015/0143999 A1    May 28, 2015

(30) Foreign Application Priority Data

Jul. 6, 2012   (EP) .................................... 12175405
Jul. 6, 2012   (EP) .................................... 12175406
(Continued)

(51) Int. Cl.
*A47J 31/00*   (2006.01)
*A23F 3/18*    (2006.01)
(Continued)

(52) U.S. Cl.
CPC ................ *A23F 3/18* (2013.01); *A23F 5/262* (2013.01); *A23L 2/52* (2013.01); *A47J 31/06* (2013.01);
(Continued)

(58) Field of Classification Search
CPC .................................................... A47J 31/4492
(Continued)

(56) References Cited

U.S. PATENT DOCUMENTS 3,975,996 A   8/1976   Vitous
4,136,202 A   1/1979   Favre
(Continued)

FOREIGN PATENT DOCUMENTS

AT   511357   11/2007
AT   511332   11/2012
(Continued)

OTHER PUBLICATIONS

Miahcel Harney, Brewing Temperature, The Harney & Sons Guide to Tea, 2008, p. 12, ., The Penguin Press.
(Continued)

*Primary Examiner* — Reginald L Alexander
(74) *Attorney, Agent, or Firm* — Foley & Lardner LLP (57) ABSTRACT

The invention provides a beverage production machine having an apparatus for recognizing a package. The apparatus comprises two resonant tank circuits, each comprising a coil and a capacitor; two electronic circuits for detecting changes in coil impedance; a means for generating a signal which is indicative of the changes; and means for controlling the beverage production machine according to the signal. The machine also comprises a holder for supporting the package. The package for use in the machine comprises a base unit having a compartment which contains tea material, and a rim with a projecting lip; conductive material associ-
(Continued)

ated with the package having two edge sections situated on opposite sides of the compartment; and a lid attached to the base unit around the rim, the central portion of the lid comprising at least one perforated line. The invention also provides a method of recognizing the package.

17 Claims, 5 Drawing Sheets

(30) Foreign Application Priority Data

| Mar. 21, 2013 | (EP) | .................... | 12160342 |
|---|---|---|---|
| Mar. 21, 2013 | (EP) | .................... | 13160324 |
| Mar. 21, 2013 | (EP) | .................... | 13160325 |
| Mar. 21, 2013 | (EP) | .................... | 13160326 |
| Mar. 21, 2013 | (EP) | .................... | 13160328 |

(51) Int. Cl.
  *B65D 85/804* (2006.01)
  *A47J 31/44* (2006.01)
  *A47J 31/06* (2006.01)
  *G01N 27/02* (2006.01)
  *A47J 31/40* (2006.01)
  *A23F 5/26* (2006.01)
  *A23L 2/52* (2006.01)
  *A47J 31/46* (2006.01)

(52) U.S. Cl.
  CPC ....... *A47J 31/0605* (2013.01); *A47J 31/0615* (2013.01); *A47J 31/0642* (2013.01); *A47J 31/407* (2013.01); *A47J 31/44* (2013.01); *A47J 31/4492* (2013.01); *A47J 31/46* (2013.01); *B65D 85/804* (2013.01); *B65D 85/8043* (2013.01); *G01N 27/025* (2013.01); *A23V 2002/00* (2013.01); *B65D 2203/00* (2013.01); *Y02W 30/807* (2015.05)

(58) Field of Classification Search
  USPC ................................. 99/295, 289 R
  See application file for complete search history.

(56) References Cited

U.S. PATENT DOCUMENTS

| 4,253,385 | A | 3/1981 | Illy |
|---|---|---|---|
| D311,138 | S | 10/1990 | Chanel |
| 4,983,410 | A | 1/1991 | Dinos |
| D322,539 | S | 12/1991 | Under |
| 5,325,765 | A | 7/1994 | Sylvan et al. |
| 5,425,480 | A | 6/1995 | Rabenau et al. |
| 5,619,904 | A | 4/1997 | Di Nunzio |
| 5,813,317 | A | 9/1998 | Ken-Hao-Chang |
| D407,640 | S | 4/1999 | Nelson et al. |
| 5,947,004 | A | 9/1999 | Huang |
| 6,009,792 | A | 1/2000 | Kraan |
| D420,856 | S | 2/2000 | Yeo et al. |
| D425,416 | S | 5/2000 | Denham et al. |
| 6,142,063 | A | 11/2000 | Beaulieu et al. |
| D436,532 | S | 1/2001 | Richardson |
| D438,103 | S | 2/2001 | Edwards et al. |
| D445,674 | S | 7/2001 | Pritchett |
| D445,675 | S | 7/2001 | Richardson |
| 6,316,753 | B2 * | 11/2001 | Clothier ............ H05B 6/06 219/621 |
| 6,382,083 | B2 | 5/2002 | Schmed |
| D462,900 | S | 9/2002 | Yamada et al. |
| D477,186 | S | 7/2003 | de Groote et al. |
| D495,189 | S | 8/2004 | Cahen |
| 6,786,134 | B2 * | 9/2004 | Green ............ A47J 31/3633 99/289 P |
| D506,926 | S | 7/2005 | Halliday et al. |
| D520,185 | S | 5/2006 | Zeng et al. |
| D539,643 | S | 4/2007 | Abel |
| D540,608 | S | 4/2007 | Cahen |
| D549,361 | S | 8/2007 | To et al. |
| D571,656 | S | 6/2008 | Maslowski |
| 7,540,232 | B2 | 6/2009 | Bates et al. |
| D602,303 | S | 10/2009 | Cahen |
| D606,363 | S | 12/2009 | Aardenburg |
| 7,640,843 | B2 | 1/2010 | Halliday et al. |
| D616,251 | S | 5/2010 | Heiberg et al. |
| D624,785 | S | 10/2010 | Rousselin |
| 7,854,192 | B2 | 12/2010 | Denisart et al. |
| D630,880 | S | 1/2011 | Zimmermann |
| D632,568 | S | 2/2011 | Caldwell et al. |
| D643,682 | S | 8/2011 | Asthon |
| 8,010,050 | B2 | 8/2011 | Kennedy |
| D649,392 | S | 11/2011 | Cahen |
| D652,718 | S | 1/2012 | Caldwell et al. |
| D659,022 | S | 5/2012 | Kemner |
| D666,451 | S | 9/2012 | Cheng |
| D670,539 | S | 11/2012 | Starr et al. |
| D672,188 | S | 12/2012 | Luippold et al. |
| 8,333,144 | B2 | 12/2012 | Boussemart et al. |
| D681,386 | S | 5/2013 | Pininfarina |
| D684,043 | S | 6/2013 | Brown et al. |
| D688,392 | S | 8/2013 | Tsai |
| D689,768 | S | 9/2013 | Inderbitzin |
| D694,620 | S | 12/2013 | Hansen |
| D697,399 | S | 1/2014 | Parmar et al. |
| 8,690,013 | B2 | 4/2014 | Kneer |
| D704,494 | S | 5/2014 | Blanc |
| 8,770,095 | B2 | 7/2014 | Pecci et al. |
| 8,820,974 | B2 | 9/2014 | Chang et al. |
| D715,465 | S | 10/2014 | Hasuo et al. |
| 8,871,285 | B2 | 10/2014 | Markoulis et al. |
| 8,993,018 | B2 * | 3/2015 | Bucher ............ A47J 31/3623 426/107 |
| D732,386 | S | 6/2015 | Paton et al. |
| 9,603,201 | B2 * | 3/2017 | Bogel ............ H05B 6/062 |
| 9,625,280 | B2 * | 4/2017 | Frese ............ G01D 5/2006 |
| 2002/0048621 | A1 | 4/2002 | Boyd et al. |
| 2002/0078831 | A1 | 6/2002 | Cai |
| 2002/0148357 | A1 | 10/2002 | Lazaris et al. |
| 2003/0033938 | A1 | 2/2003 | Halliday et al. |
| 2005/0015348 | A1 | 1/2005 | Knepler |
| 2005/0172822 | A1 | 8/2005 | Macchi et al. |
| 2005/0236323 | A1 | 10/2005 | Oliver et al. |
| 2006/0065127 | A1 | 3/2006 | Dalton et al. |
| 2006/0174770 | A1 | 8/2006 | Jordana |
| 2008/0072766 | A1 | 3/2008 | Kobylarz |
| 2008/0105130 | A1 | 5/2008 | Koeling et al. |
| 2008/0148948 | A1 | 6/2008 | Evers et al. |
| 2009/0155422 | A1 | 6/2009 | Ozanne |
| 2009/0220650 | A1 | 9/2009 | Ozanne |
| 2010/0055252 | A1 | 3/2010 | Marina et al. |
| 2010/0132564 | A1 | 6/2010 | Ozanne et al. |
| 2010/0154644 | A1 | 6/2010 | Skalski et al. |
| 2010/0173056 | A1 | 7/2010 | Yoakim et al. |
| 2010/0180775 | A1 | 7/2010 | Kollep et al. |
| 2010/0239734 | A1 | 9/2010 | Yoakim et al. |
| 2010/0263546 | A1 | 10/2010 | Leuzinger et al. |
| 2010/0288131 | A1 | 11/2010 | Kilber et al. |
| 2011/0052761 | A1 | 3/2011 | Yoakim et al. |
| 2011/0303095 | A1 | 12/2011 | Fu et al. |
| 2011/0308399 | A1 | 12/2011 | Jung |
| 2012/0070543 | A1 | 3/2012 | Mahlich |
| 2012/0098526 | A1 | 4/2012 | Bucher et al. |
| 2013/0095212 | A1 | 4/2013 | Beer |
| 2013/0119930 | A1 * | 5/2013 | Sakoda ............ B60L 11/182 320/108 |
| 2013/0129872 | A1 * | 5/2013 | Kruger ............ A47J 31/4492 426/115 |
| 2013/0302476 | A1 | 11/2013 | Abegglen et al. |
| 2014/0196608 | A1 | 7/2014 | Amrein et al. |
| 2014/0272016 | A1 | 9/2014 | Nowak |
| 2014/0356484 | A1 | 12/2014 | Capitani |
| 2015/0143999 | A1 | 5/2015 | Cross et al. |
| 2015/0173558 | A1 | 6/2015 | Cross et al. |

(56) References Cited

U.S. PATENT DOCUMENTS

| | | |
|---|---|---|
| 2015/0190010 A1 | 7/2015 | Cross et al. |
| 2015/0203285 A1 | 7/2015 | Baldo |
| 2015/0239655 A1 | 8/2015 | Schroeder et al. |
| 2016/0045059 A1 | 2/2016 | Cross et al. |
| 2016/0114967 A1 | 4/2016 | Van Belleghem et al. |
| 2016/0270580 A1 | 9/2016 | Smith |

FOREIGN PATENT DOCUMENTS

| | | |
|---|---|---|
| CA | 289071 | 10/2012 |
| CN | 2636781 | 9/2004 |
| CN | 2636781 | 11/2004 |
| CN | 101056561 | 10/2007 |
| DE | 202014104474 | 1/2013 |
| EP | 0334573 | 9/1989 |
| EP | 0451980 | 3/1991 |
| EP | 0455337 | 3/1991 |
| EP | 0554469 | 8/1993 |
| EP | 1654966 | 10/2004 |
| EP | 1772081 | 10/2005 |
| EP | 1658796 | 5/2006 |
| EP | 1772398 A1 | 10/2006 |
| EP | 1922962 | 11/2006 |
| EP | 1774878 | 4/2007 |
| EP | 1849718 | 10/2007 |
| EP | 1937115 | 7/2008 |
| EP | 2263501 | 12/2010 |
| EP | 2243378 B1 | 6/2011 |
| EP | 2476633 | 7/2012 |
| GB | 1561188 | 2/1980 |
| GB | 2437483 | 4/2006 |
| GB | 2485575 | 5/2013 |
| JP | 5376171 | 7/1978 |
| JP | 54161781 | 11/1979 |
| JP | 57140239 | 9/1982 |
| JP | 10275275 | 10/1998 |
| RU | 2192140 | 11/2002 |
| WO | WO2006038227 | 4/2006 |
| WO | WO2007019993 | 2/2007 |
| WO | WO07042486 | 4/2007 |
| WO | WO2007042415 | 4/2007 |
| WO | WO2007042485 | 4/2007 |
| WO | WO2008025730 | 3/2008 |
| WO | WO2008058576 | 5/2008 |
| WO | WO2008156283 | 12/2008 |
| WO | WO2009130311 | 10/2009 |
| WO | WO2010076263 | 7/2010 |
| WO | WO2011000723 | 1/2011 |
| WO | WO2011000724 | 1/2011 |
| WO | WO2011000725 | 1/2011 |
| WO | WO2011141532 | 11/2011 |
| WO | WO2012010317 | 1/2012 |
| WO | WO2012072508 | 6/2012 |
| WO | WO2013008012 | 1/2013 |
| WO | WO2012144885 | 10/2013 |

OTHER PUBLICATIONS

Search Report in EP15180266, dated Dec. 9, 2015.
Written Opinion in EP15180266, dated Dec. 9, 2015.
IPRP2 in PCTEP2013063947, dated Nov. 21, 2014.
Copending application for Blanc, U.S. Appl. No. 29/440,100, filed Dec. 9, 2012.
Copending application for Paton et al., U.S. Appl. No. 29/466,849, filed Sep. 12, 2013.
Copending application for Paton et al., U.S. Appl. No. 29/466,853, filed Sep. 12, 2013.
Copending application for Cross et al., U.S. Appl. No. 14/408,623, filed Dec. 17, 2014.
Copending application for Bittar, U.S. Appl. No. 14/408,634, filed Dec. 17, 2014.
Copending application for Cross et al., U.S. Appl. No. 14/408,624, filed Dec. 17, 2014.
Copending application for Cross et al., U.S. Appl. No. 14/408,635, filed Dec. 17, 2014.
Copending application for Cross et al., U.S. Appl. No. 14/408,639, filed Dec. 17, 2014.
Copending application for Cross et al., U.S. Appl. No. 14/408,638, filed Dec. 17, 2014.
Search Report & Written Opinion in EP15188381, dated Feb. 1, 2016.
Jan. 1, 2013, Espresso Coffee Club Nespresso Swiss Capsules 2013 p. 1, p. 1.
Oct. 7, 2014, IPRP2 in PCTEP2013063942.
CBTL Caffitaly E Caffe Capsules 2013 p. 1, Jan. 1, 2013, p. 1.
IPRP2 in PCTEP2013063950, dated Jul. 6, 2014.
Nespresso Single Serve Capsules 2013 p. 1, Jan. 1, 2013, p. 1.
Search Report in EP12175405, dated Jan. 24, 2013.
Search Report in EP12175406, dated Dec. 21, 2012.
Search Report in EP14159168, dated Jun. 24, 2014.
Search Report in PCTEP2013063942, dated Feb. 11, 2014.
Search Report in PCTEP2013063943, dated Feb. 7, 2014.
Search Report in PCTEP2013063946, dated Feb. 6, 2014.
Search Report in PCTEP2013063947, dated Mar. 24, 2014.
Search Report in PCTEP2013063948, dated Mar. 24, 2014.
Search Report in PCTEP2013063949, dated Feb. 6, 2014.
Search Report in PCTEP2013063950, dated Feb. 7, 2014.
Search Report in PCTEP2014054859, dated Jul. 2, 2014.
Written Opinion in EP12175405, dated Jan. 24, 2013.
Written Opinion in EP12175406, dated Dec. 21, 2012.
Written Opinion in PCTEP2013063942, dated Feb. 11, 2014.
Written Opinion in PCTEP2013063943, dated Feb. 7, 2014.
Written Opinion in PCTEP2013063946, dated Feb. 6, 2014.
Written Opinion in PCTEP2013063947, dated Mar. 24, 2014.
Written Opinion in PCTEP2013063948, dated Mar. 24, 2014.
Written Opinion in PCTEP2013063949, dated Feb. 6, 2014.
Written Opinion in PCTEP2013063950, dated Feb. 7, 2014.
Written Opinion in PCTEP2014054859, dated Jul. 2, 2014.
Definition of Intersect, Merriam-Webster Dictionary, 2017, 1 Page.
Search Report & Written Opinion in EP17155955, dated May 22, 2017.
Definition for Contain, Dictionary.com, Jun. 27, 2017, pp. 1-4.
Measuring and Memory Systems, KamanInductive Technology Handbook, 2012, pp. 1-39.
Stephen A. Dyer, In-depth coverage of instrumentation and measurement from the Wiley Encyclopedia of Electrical, Wiley Survey of Instrumentation and Measurement, 2017, pp. 1-5.

\* cited by examiner

PACKAGE RECOGNITION SYSTEM

TECHNICAL FIELD OF THE INVENTION

The present invention relates to a recognition system for a package. In particular the invention relates to a coding system which allows the recognition of a package, for example in a beverage production machine. The invention also relates to a method and an apparatus for recognising such a package.

BACKGROUND OF THE INVENTION

Automated beverage production machines which are designed to use portioned ingredients are already known. Often such machines use packages (e.g. capsules, cartridges, pods) containing a predetermined dose of beverage ingredient (e.g. ground coffee, cocoa powder, tea leaves). Such packages are convenient to use and can facilitate the preparation of beverages that are consistent in terms of taste and quality.

The working parameters of beverage production machines may need to be varied according to the type of beverage being prepared. This can be achieved by associating a particular type of package with a set of machine parameters. Several systems for recognising packages have been proposed.

European patent application EP 0 451 980 (Kraft General Foods Limited) relates to packages containing comestibles for the preparation of beverages, which are preferably provided with a recognition means. Several possible systems are postulated, each comprising a particular recognition means and appropriate sensor. For example, the recognition means may comprise one or more surface features formed in the body of the package which can be identified by a mechanical sensor or an optical sensor; one or more strips of a magnetic material applied to the body of the package which can be read by an appropriate magnetic sensor; one or more shaped or divided areas of metal foil applied to the package body which cause an inductive effect on movement of the package in the machine, which inductive effect can be sensed; or one or more electrically conductive areas formed on the body of the package which can be sensed electronically.

International patent application WO 2011/141532 (Nestec S.A.) describes a capsule, system and method for preparing a beverage by centrifugation. The capsule comprises a code arranged to be read while the capsule is rotated around an axis of rotation traversing the capsule. Optical reading of a code that has been applied on the capsule by printing, embossing or laser engraving is preferred. Inductive sensing of a code formed by reliefs or recesses provided on a circumferential metal rim of the capsule is also disclosed.

International patent application WO 2012/010317 (Krüger GmbH & Co. KG) concerns beverage capsules that can only be used in one particular automatic coffee machine. The capsules have an identifying mark which is scanned by the coffee machine; several possible embodiments of identifying mark are suggested. For example, the identifying mark may comprise: regions with differing optical reflection characteristics, an indentation and/or a protrusion, a printed item such as a barcode, a fluorescent region, an electrically conducting region, a metallic region, a ferromagnetic region, or a radiofrequency identification (RFID) chip.

A problem with identifying a package in a beverage production machine is that retrieving or reading information from the package is not always reliable or convenient. For example, it is often necessary to use a coding system with a high level of redundancy in order to ensure that the package can be read while it is moving and/or in situations wherein the environment around the package is not clean (e.g. due to the presence of residual beverage ingredient). Furthermore, in order for a package to be correctly identified, it is often necessary for the package to be aligned or positioned within the beverage production machine in a precise manner. It is an object of the present invention to overcome these disadvantages.

SUMMARY OF THE INVENTION

In a first aspect, the present invention relates to a beverage production machine comprising apparatus for recognising a package, the apparatus comprising:
  two resonant tank circuits, each one comprising a coil and
    a capacitor;
  two electronic detection circuits for detecting changes in
    coil impedance;
  a means for generating a signal wherein the signal is
    indicative of the changes in coil impedance; and
  a control means for controlling at least one parameter of
    the beverage production machine according to the
    signal;
the beverage production machine further comprising a package holder for supporting the package within the machine.

This arrangement recognises the package using the principle of electromagnetic induction and metal detection. The presence of two coils improves the robustness of the recognition system with respect to physical tolerances (e.g. alignment of the package within the apparatus). This permits recognition of coded packages in a simple yet reliable manner and reduces the time required to identify a particular package and/or increases the accuracy of the identification.

In a second aspect, the invention relates to a package for a beverage production machine, the package comprising:
  a base unit having a compartment which contains tea
    material, and a rim;
  conductive material associated with the package; the
    conductive material having two edge sections which
    are situated on opposite sides of the compartment; and
  a lid attached to the base unit around the rim so as to
    enclose the tea material within the package, the lid
    comprising:
    a central lidding portion comprising at least one perforated line.

The edge sections of the conductive material encode information which allows the beverage production machine to recognise the package. Furthermore, the coding system can tolerate some variation in the positioning of the package within the beverage production machine, or in the positioning of the conductive material on the package.

In a preferred embodiment the package of the second aspect comprises:
  a base unit having a compartment which contains tea
    material, and a rim with a projecting lip extending
    partially or wholly around the rim;
  conductive material associated with the projecting lip; the
    conductive material having two edge sections which
    are situated on opposite sides of the compartment; and
  a lid attached to the base unit around the rim so as to
    enclose the tea material within the package, the lid
    comprising:
    a peripheral portion overlaying the projecting lip; and
    a central lidding portion comprising at least one perforated line.

In use, the beverage production machine of the first aspect of the invention contains a package according to the second aspect of the invention.

In a third aspect, the invention relates to a method of recognising a package according to the second aspect of the invention in a beverage production machine according to the first aspect of the invention, the method comprising:

placing the package in the package holder;
applying alternating current to two coils while the package is stationary, the coils being positioned in the beverage production machine such that they generate eddy currents within the conductive material adjacent to the edge sections;
detecting a change in coil impedance for each of the coils;
generating a signal indicative of the change in impedance; and
identifying the package according to the signal.

The method of the invention permits near field and non-contact detection of the packages, and is particularly suitable in instances where the beverage production machine needs to recognise a limited number of codes (i.e. preferably no more than 10 codes). An advantage of this method is that the coils do not need to be in physical contact with the conductive material. This means that package recognition is possible even if there is water and/or residual tea material between the coil and the package. Furthermore, this method allows recognition of a package which is encoded with a simple coding system over a wide range of physical and electrical tolerances. Since the package is stationary within the beverage production machine during recognition, the method can be carried out by an apparatus with reduced complexity (e.g. comprising fewer components) which is envisaged to be economic to manufacture.

DETAILED DESCRIPTION

As used herein the term "comprising" encompasses the terms "consisting essentially of" and "consisting of". All percentages and ratios contained herein are calculated by weight unless otherwise indicated. It should be noted that in specifying any range of values or amount, any particular upper value or amount can be associated with any particular lower value or amount.

The disclosure of the invention as found herein is to be considered to cover all embodiments as found in the claims as being multiply dependent upon each other irrespective of the fact that claims may be found with multiple dependency or redundancy.

As used herein the term "tea material" refers to tea plant material, herb plant material or a mixture thereof. For the avoidance of doubt, the term "tea material" does not include coffee material. The term "tea plant material" refers to leaf, bud and/or stem material from *Camellia sinensis* var. *sinensis* and/or *Camellia sinensis* var. *assamica*. The tea plant material may be substantially fermented (i.e. black tea), partially fermented (i.e. oolong tea) or substantially unfermented (i.e. green tea or white tea). It may also be a blend of one or more of the aforementioned tea plant materials. Other ingredients which are commonly used to flavour leaf tea products may also be combined with the tea plant material (e.g. bergamot, citrus peel and the like). The term "herb plant material" refers to material which is commonly used as a precursor for herbal infusions. Preferably the herb plant material is selected from chamomile, cinnamon, elderflower, ginger, hibiscus, jasmine, lavender, lemongrass, mint, rooibos (obtained from *Aspalathus linearis*), rosehip, vanilla and *verbena*. The tea material may additionally comprise fruit pieces (e.g. apple, blackcurrant, mango, peach, pineapple, raspberry, strawberry etc).

Preferably the tea material is dried and has a moisture content of less than 30 wt %, preferably less than 20 wt % and most preferably from 0.1 to 10 wt %. Preferably the tea material particles have a size (i.e. longest diameter) of from about 2 to about 10 mm, preferably 3 to 7 mm.

The term "beverage" refers to a substantially aqueous drinkable composition which is suitable for human consumption. Preferably the beverage comprises at least 85% water by weight of the beverage, more preferably at least 90% and most preferably from 95 to 99.9%. Preferably the beverage comprises from 0.04 to 3%, more preferably from 0.06 to 2%, most preferably from 0.1 to 1% by weight tea solids.

The term 'brewing' refers to the addition of a liquid, particularly hot water, to tea material, so that steeping or soaking the team material in the liquid releases soluble substances into the liquid (e.g. flavour and/or aroma molecules) thereby to form a beverage. Brewing may be carried out at any temperature, but preferably in the range of 80 to 95° C.

As used herein the term "package" refers to a rigid or semi-rigid container in which tea material is or may be packaged. For example the package can be a capsule, cartridge, pod, or the like.

The apparatus for recognising a package in a beverage production machine comprises:

two resonant tank circuits, each one comprising a coil and a capacitor;
two electronic detection circuits for detecting changes in coil impedance;
a means for generating a signal wherein the signal is indicative of the changes in coil impedance; and
a control means for controlling at least one parameter of the beverage production machine according to the signal.

Each resonant tank circuit comprises a coil and a capacitor, and is designed to resonate at a frequency that induces eddy currents in a conductive material. Preferably each tank circuit is designed to resonate at a frequency of 50 to 200 kHz, more preferably 75 to 150 kHz. Preferably the coils are spaced apart by a distance of from 40 to 50 mm, more preferably from 45 to 47 mm, because this corresponds to a convenient package size.

Each electronic detection circuit monitors the change in coil impedance and derives a signal indicative of the change in coil impedance. Further characteristics of the signal may be extracted by electronic and/or software processing. Since the amplitude of the signal is typically inversely proportional to the proximity of the conductive material to the coil, preferably the coil and the conductive area are separated by a distance of 0 to 2 mm, more preferably 0 to 1 mm.

Identification of the package preferably controls at least one parameter of the beverage production machine. Thus in a preferred embodiment the control means controls one or more of: the temperature, pressure, volume or flow rate of the brewing liquid, the path(s) the brewing liquid follows within the beverage production machine and/or the brewing time.

The beverage production machine also comprises a package holder which supports the package within the machine and preferably interacts with the package to direct the location and alignment of the package within the beverage production machine.

The package comprises a base unit, preferably a cup-shaped base unit, having a rim preferably with a projecting lip extending wholly or partially around the rim. The base unit defines a compartment which encloses tea material. To aid sealing of the tea material within the package, in a preferred embodiment the projecting lip extends wholly around the rim. In order to facilitate efficient and cost-effective manufacture, it is preferred that the base unit is formed as a single piece, for example by injection moulding or by thermoforming. Preferably the base unit is made from a non-conductive material such as food-grade plastic, for example polypropylene. The package needs to be large enough to contain a single serving of the dry tea material. Thus the internal volume of the package (i.e. the volume of the compartment) is preferably from 10 to 24 $cm^3$, more preferably 12 to 19 $cm^3$, most preferably from 14 to 18 $cm^3$. The compartment should not be so shallow that tea material bounces out of it during filling. Thus the depth of the compartment is preferably at least 10 mm, more preferably at least 13 mm. On the other hand, the compartment should not be so deep that it is difficult to remove the tea material from the capsule at the start of brewing. Thus the depth of the compartment is preferably at most 20 mm, more preferably at most 18 mm. It is easier to remove the tea material from a compartment with a depth in the upper part of this range when the volume of the cavity is also towards the upper end of its range (i.e. when the cavity is not both deep and narrow). The cross-sectional area and diameter of the compartment are related to the required volume and depth. Consequently, the diameter of the compartment is preferably from 30 to 45 mm. In certain preferred embodiments, the base unit is shaped so as to direct the alignment of the package within the beverage production machine, and the package holder is adapted accordingly to ensure that it interacts with the shaped base unit. It is particularly preferred that the projecting lip is shaped so as to direct the alignment of the package within the beverage production machine. Preferably the package can be aligned within the beverage production machine in any one of n fixed orientations, wherein n is an integer. Preferably n is 1, 2, 3, or 4, more preferably n is 1 or 2 and most preferably n is 2. In an especially preferred embodiment, the base unit has a generally circular cross-section, but the projecting lip is elongated, for example elliptical in shape, or is defined by two intersecting circular arcs; the ratio of the longest diameter of the lip to the shortest diameter of the lip is preferably from 1.2:1 to 1.5:1.

In addition to the base unit, the package comprises a lid. The lid is attached to the base unit around the rim so as to enclose the tea material within the package. The lid may be attached to the base unit by any suitable means, for example by gluing or heat sealing. In a preferred embodiment, the lid consists of a peripheral portion and a central lidding portion. The peripheral portion of the lid extends outwards from the rim of the base unit and overlays at least part of (but preferably not all of) the projecting lip, whereas the central lidding portion extends inwards from the rim of the base unit and covers the tea material.

The central lidding portion of the lid comprises at least one perforated line. The perforated line facilitates opening of the package lid along the line, thereby allowing release of the tea material from the package, for example by pressing an opening member against the lid close to the perforated line. As used herein the term "perforated line" refers to an organised arrangement of slits. The perforated line is preferably a curved line located part way between the edge of the central lidding portion and the centre of the central lidding portion, with the curve facing towards the centre of the lidding portion. The cut:tie ratio of the perforations should be such that they do not burst too easily, for example during transit, but nonetheless open without requiring too great a force. For example, a cut:tie ratio of around 1:2 is suitable. Embodiments wherein the lid comprises a plurality of perforated lines are also envisaged. For example, the lid may comprise a symmetrical arrangement of two perforated lines.

The package comprises a conductive material, which is preferably associated with the projecting lip. The conductive material has two edge sections situated on opposing sides of the compartment. The edge sections are preferably situated near to or at opposite ends of the projecting lip i.e. near to or at opposite ends of the package. The conductive material encodes information so that the package is recognised in a beverage production machine according to the configuration of the conductive material. The conductive material can be associated with the projecting lip in a number of different ways, and several preferred embodiments are described below. Preferred examples of conductive materials include metallic sheets (especially metallic foils), conductive inks and wire loops. Metallic sheets and more particularly metallic foils or foil laminates are especially preferred, since they are easy to cut and shape.

Preferably, at least part of the peripheral portion of the lid comprises the conductive material. Preferably the conductive material comprises metallic foil, more preferably aluminium foil. The foil may be of any thickness, although a foil having a thickness of 10 to 100 μm is particularly preferred. It is not necessary for the foil to be smooth. In fact, in order to allow the seal between the lid and the base unit to be controlled (e.g. in terms of seal strength) in certain embodiments the metallic foil is embossed. It is also envisaged that the lid can be a polymer/metallic foil laminate. Most preferably, the whole lid (i.e. the central lidding portion and the peripheral portion) comprises conductive material.

Nevertheless it will be appreciated that it is not necessary for the entire lid to consist of the conductive material. For example, embodiments are also envisaged wherein the lid comprises a polymer film with one or more metallic strips positioned on the lid so that the edge sections of the conductive material are situated on opposite sides of the compartment, near to or at opposite ends of the lid.

A package embodiment wherein the conductive material is not an integral part of the lid is also envisaged. Thus the conductive material may be associated with the lip without being an integral part of the lid. For example, the conductive material may comprise a conductive material placed on top of a non-conductive lid (e.g. as a sticker) or between the projecting lip and the lid.

In an alternative embodiment wherein the conductive material is associated with the lip without being part of the lid, the projecting lip has an underside and the conductive material is associated with the underside of the projecting lip, whereas the lid is attached to the upper side of the projecting lip. Therefore, in this embodiment the lid need not comprise conductive material, and preferably consists of a non-conductive material, more preferably a plastic film. The conductive material may be physically attached to the underside of the projecting lip (e.g. by gluing, heat sealing etc). In such an embodiment it is preferred that the conductive material is flexible (e.g. metallic foil) so as to ensure a close fit with the underside of the projecting lip. However alternative embodiments wherein the conductive material is releasably associated with the underside of the projecting lip are also envisaged. For example, the conductive material may consist of a metallic sheet comprising a central opening shaped so as to releasably engage with the base unit. The conductive material may rest on or be attached to the package holder, so that the projecting lip of the package rests on and becomes associated with the conductive material when the package is inserted into the package holder of the beverage production machine.

In a further embodiment wherein the conductive material is associated with the lip without being part of the lid, the projecting lip itself comprises the conductive material. For example the projecting lip is made from conductive material or the projecting lip is made from non-conducting material with conductive material encased within it.

It is preferred that edge sections are substantially straight-edged sections, and it is particularly preferred that the edge sections are parallel to one another. The edge sections do not need to extend across the entire width of the projecting lip, but in a preferred embodiment they do. This embodiment is especially tolerant to variations in the positioning of the package within the beverage production machine.

In a very preferred embodiment, the lid is a metal foil or a polymer/metal foil laminate. The edge sections are substantially straight-edged sections, which are parallel to one another and extend across the entire width of the package lid, so that the lid is truncated, compared to the projecting lip, such that the peripheral portion of the lid does not overlay the whole of the projecting lip. The truncation of course must not encroach into the central lidding portion, as this would compromise the seal between the lid and the base unit. Preferably the length of the lid between the edge sections is from 45 to 60 mm, more preferably from 47 to 58 mm, and the maximum width of the lid is from 45 to 50 mm, because these correspond to a convenient package size and aesthetic shape The packages described above are coded and recognition of these packages is based on the principle of electromagnetic induction and metal detection. This permits recognition of the coded packages in a simple yet reliable manner. The packages are designed to be identified by an apparatus comprising two coils. However for the sake of clarity, the principle of recognition is initially explained below with reference to a single coil.

A coil carrying an alternating current and located in the beverage production machine close to the package induces eddy currents in the conductive material. The eddy currents produce an opposing electromagnetic flux that changes the impedance of the coil. The change in impedance is a function of the strength and freedom of the eddy currents to circulate within the conductive material. Discontinuities in the conductive material constrain and weaken the strength of the eddy currents and affect the impedance of the coil.

In the present invention, the arrangement of the edge sections determines the nature (e.g. position, shape) of the boundaries of the conductive material These boundaries represent discontinuities in the conductive material. Thus the package has a code which can be identified using a recognition system based on eddy current sensing.

An advantage of recognising of packages in this way is that the coils do not need to be in physical contact with the conductive material of the package. This means that package recognition is possible even if there is a non-conductive material between the coil and the conductive material. This is the reason that several ways of associating the conductive material with the projecting lip are possible. Furthermore, the presence of water and/or residual tea material between the coil and the conductive material does not prevent package recognition.

Typically the packages are provided to the consumer in air-tight secondary packaging, for example as multipacks containing a plurality of packages (e.g. ten). The multipacks may contain packages of a single type, or a mixture of packages containing different types of tea (e.g. green tea, black tea, herbal tea) and having different codes according to the type of tea that each contains. The perforated lid has the advantage that some of the tea aroma is released from the tea material inside the capsule into the space inside the secondary packaging. Thus the consumer obtains the aroma of tea on opening the secondary pack.

The method of recognising the package described above in the beverage production machine described above comprises:

placing the package in the package holder;
applying alternating current to two coils while the package is stationary, the coils being positioned in the beverage production machine such that they generate eddy currents within the conductive material adjacent to the edge sections;
detecting a change in coil impedance for each of the coils;
generating a signal indicative of the change in impedance; and
identifying the package according to the signal.

This method enables a single beverage production machine to prepare a number of different beverages which require different preparation conditions. It is particularly suitable where the beverage production machine needs to recognise a limited number of codes (preferably no more than 10 codes). In a preferred embodiment the package is identified by comparing the signal with a number of reference signals, each one corresponding to a certain type of package. For example, it is envisaged that each type of package may contain a particular tea material. As such a package containing green tea would be recognised as a different type of package requiring different brewing conditions to a package containing black tea.

Identification of the package preferably controls at least one parameter of the beverage production machine, e.g. the temperature, pressure, volume or flow rate of the brewing liquid, the path(s) the brewing liquid follows within the beverage production machine and/or the brewing time.

FIGURES

Figure 1:
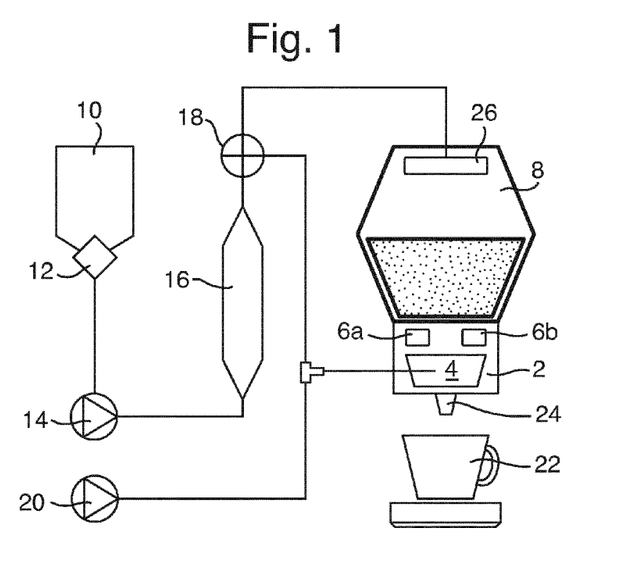
FIG. 1 is a schematic diagram showing basic components of a beverage production machine.

By way of example, certain embodiments of the invention are illustrated by the figures, in which:

FIG. 1 is a representation of the basic set up of a beverage production machine. The method of the present invention can be used to recognise a package in such a machine.

The beverage production machine comprises a holder 2, which can receive a package 4. The package comprises an area of conductive material (not shown). Two coils 6a, 6b are positioned in close proximity (preferably 0 to 2 mm) to the conductive material. This arrangement facilitates recognition of the package as described above.

The beverage production machine preferably comprises a brewing chamber 8. Water from a reservoir 10 is fed to the brewing chamber 8 via a water filter 12, a water pump 14, a heater 16 and a valve 18. The valve 18 controls the route the water takes between the heater 16 and the brewing chamber 8. In order to produce a beverage, water from the reservoir 10 preferably enters the brewing chamber 8 via the package 4. An air pump 20 pumps air along with the water and thus facilitates the mixing of the package contents with the water. The beverage can subsequently be dispensed into a receptacle 22 (e.g. cup, mug) via a spout 24. In order to rinse and/or clean the brewing chamber 8, the valve 18 can re-direct the water such that it enters the brewing chamber 8 via a rinse head 26.

Figure 2A:
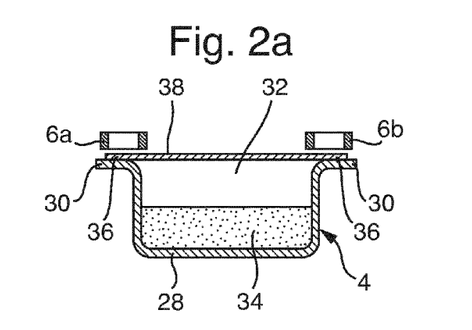
FIG. 2a shows a cross-sectional view of a package in a preferred reading mode.

FIG. 2a shows a cross-sectional side view of a package in a preferred reading mode in the beverage production machine. The package 4 comprises a base unit 28 having a rim and a projecting lip 30. The base unit 28 defines a compartment 32 which encloses tea material 34. The package 4 also comprises a lid which consists of a peripheral portion 36 overlaying part (but not all) of the projecting lip 30 and a central lidding portion 38 which covers the compartment 32. In the embodiment shown the projecting lip 30 extends wholly around the rim. The lid is attached to the base unit around the rim, thus sealing the tea material 34 within the package. In the embodiment shown, the whole of the base unit (including the projecting lip 30) is formed from a non-conductive material (e.g. plastic) and the entire lid (i.e. peripheral portion 36 and central lidding portion 38) comprises a conductive material (e.g. metallic foil, for example a laminate of aluminium foil and polyethylene). The beverage production machine has two coils 6a, 6b which are shown positioned above the package 4.

Figure 2B:
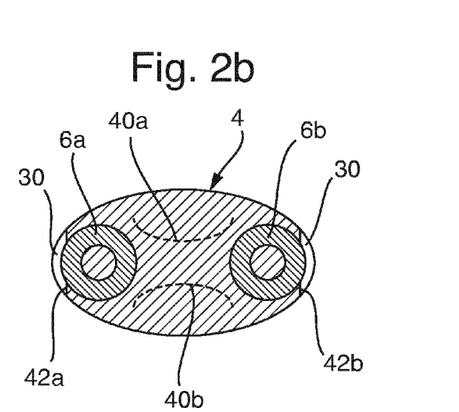
FIG. 2b shows the package of FIG. 2a viewed from above.

FIG. 2b shows the package of FIG. 2a viewed from above. In the embodiment shown, the central lidding portion 28 comprises two perforated lines 40a, 40b. The lid is the same size and shape as the projecting lip, except that it is truncated at either end, so that the peripheral portion of the lid does not overlay the whole of the projecting lip. The truncated ends form the two edge sections 42a, 42b which are situated near to opposite ends of the lid. Each edge section constitutes a boundary of the conductive material of the lid. One edge section 42a is situated beneath coil 6a and the other edge section 42b is situated beneath coil 6b.

Figure 2C:
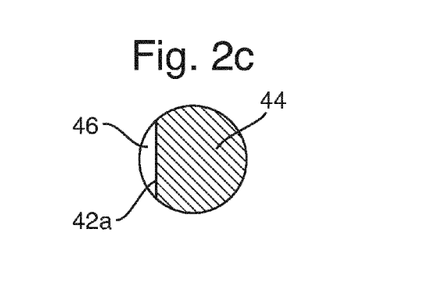
FIG. 2c is a more detailed view of part of the package of FIG. 2b.

The area of the package beneath coil 6a is illustrated in FIG. 2c. It will be appreciated that this area consists of a conductive area 44 (provided by the lid) and a non-conductive area 46 (provided by the projecting lip). The boundary of the conductive area 44 is defined by the edge section 42a. Thus the two coils (6a, 6b) are positioned such that they generate eddy currents within the conductive areas 44 traversed by the edge sections 42a, 42b.

Figure 3:
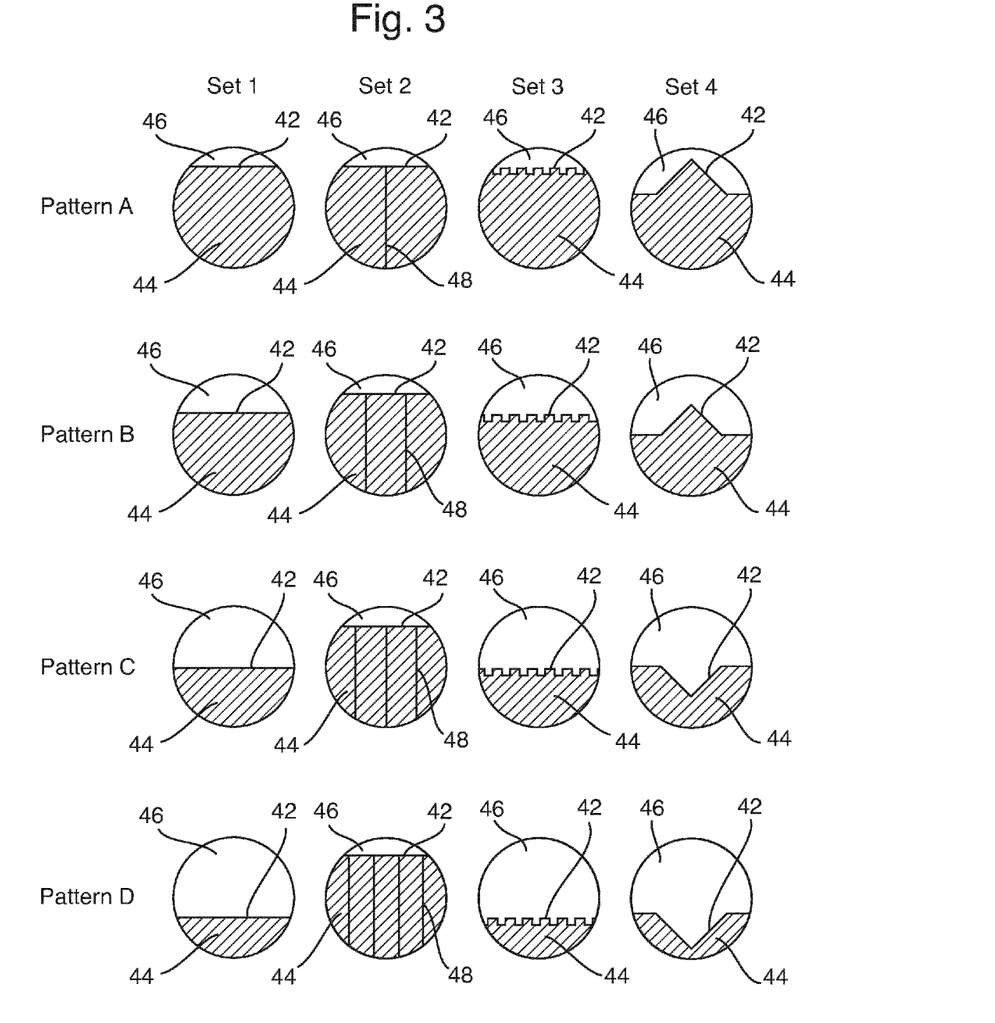
FIG. 3 illustrates several examples of possible coding patterns.

FIG. 3 illustrates several examples of possible coding patterns wherein an edge section 42 defines a boundary of an area of conductive material 44. In each case, the areas shown represent the area that is beneath the coil during package identification. For the sake of convenience, these embodiments are illustrated as 4 code sets, with each code set consisting of 4 patterns (pattern A, pattern B, pattern C, pattern D). However, this is not meant to imply that these sets are in any way limiting. For example a code set could be compiled by selecting each of patterns A, B, C and D from set 1 or by selecting pattern A from set 1, pattern B from set 2, pattern C from set 3 and pattern D from set 4. In fact any combination is possible, so long as each of pattern A, pattern B, pattern C and pattern D is associated with a unique and identifiable change in coil impedance. Each of the patterns consists of an area of conductive material 44. For example, the patterns may comprise plastic overlaid with metallic foil, metallic foil overlaid with plastic or metallic foil enclosed within plastic. The edge section 42 can be a substantially straight-edged section (e.g. as in set 1 and set 2). However this is not necessarily the case, for example the edge section 42 can alternatively comprise one or more notches (e.g. as in set 3 and set 4).

As described above, discontinuities in the conductive material 44 constrain and weaken the strength of the eddy currents and affect the impedance of the coils 6a, 6b. The edge sections 42 constitute discontinuities in the conductive material 44. For example, patterns A to D in set 1 differ in that the position of the edge section 42 varies. Pattern A comprises a greater proportion of conductive material 44 than pattern B, therefore the strength of the eddy currents generated in the conductive material 44 of pattern B will be weaker than the eddy currents generated in the conductive material 44 of pattern A. Thus each of pattern A and pattern B is associated with a unique and identifiable change in coil impedance.

As well as or in addition to the edge of the conductive material, the patterns may comprise other discontinuities (e.g. slits, perforations, folds, creases, etc) that are arranged in a predetermined manner. For example, in set 2 the position of the edge section 42 is constant in patterns A to D. These patterns all comprise a predetermined arrangement of slits 48 formed in the conductive material 44. The arrangement of the slits 48 serves to constrain and weaken the strength of the eddy currents generated in the conductive material 44. Thus once again, each of patterns A to D of set 2 is associated with a unique and identifiable change in coil impedance.

Figure 4A:
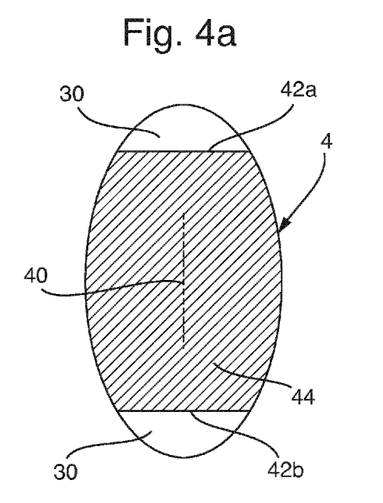
FIGS. 4a to 4d illustrate four different package embodiments wherein each package is coded with the same pattern.

FIGS. 4a to 4d illustrate four different package embodiments wherein the lid of each package is coded with the same pattern. In FIG. 4a the package lid is a metallic foil lid that is truncated across its entire width. In fact the lid is truncated at each end in a symmetrical manner. In this embodiment, the edge sections 42a, 42b situated near to the opposite ends of the lid are substantially straight and extend across the entire width of the package lid. As such, when this package is inserted into the beverage production machine, the pattern beneath coil 6a is the same as the pattern beneath coil 6b.

Figure 4B:
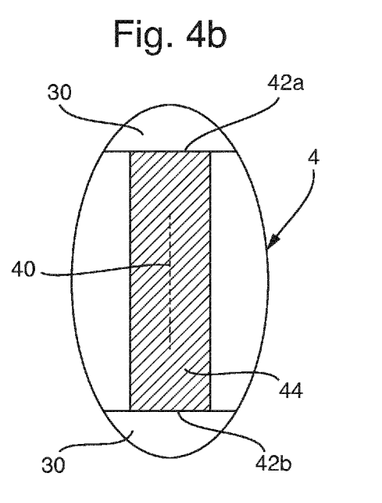

The package represented in FIG. 4b has a lid that comprises a metallic foil stripe laminated to a polymer film. The lid is truncated at each end in a symmetrical manner. When this package is inserted into the beverage production machine, the pattern beneath coil 6a is the same as the pattern beneath coil 6b. In this embodiment, the edge sections 42a, 42b of the conductive material (i.e. the foil stripe) do not extend across the entire width of the package, even though the lid itself is truncated across its entire width.

Figure 4C:
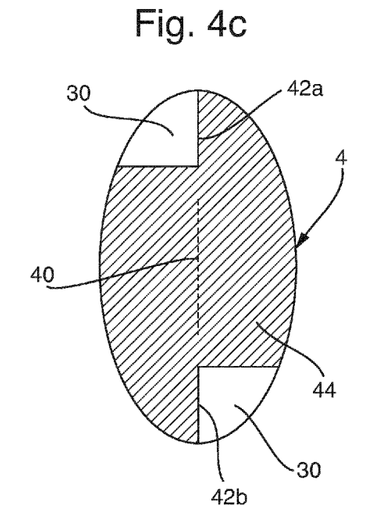

In FIG. 4c the package comprises a metallic foil lid which is truncated across only part of its width. When this package is inserted into the beverage production machine, the pattern beneath coil 6a is the same as the pattern beneath coil 6b. However, it should be appreciated that the relevant edge sections 42a, 42b (i.e. those beneath the coils) in this embodiment are perpendicular to those as represented in the embodiments shown in FIGS. 4a, 4b and 4d.

Figure 4D:
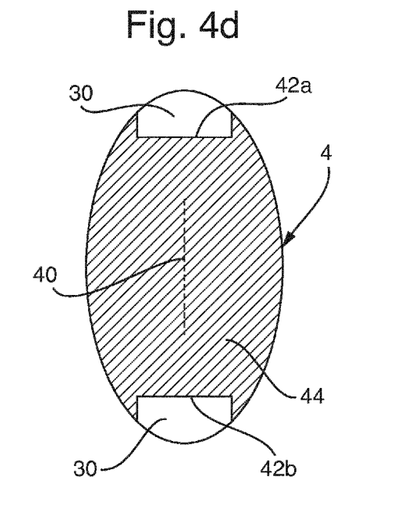

FIG. 4d shows a further embodiment wherein the metallic foil lid is shaped such that it is truncated across only part of its width. As such the edge sections 42a, 42b situated near to the opposite ends of the lid do not extend across the entire width of the package. When this package is inserted into the beverage production machine, the pattern beneath coil 6a is the same as the pattern beneath coil 6b.

FIGS. 5a to 5e illustrate the effect of variations in package placement within the beverage production machine or in the placement of the conductive material on the package. The packages represented in each of FIGS. 5a to 5e are identical, and are coded such that they have the same pattern at each end of the package lid.

In these embodiments the coding system corresponds to set 1 in FIG. 3, with an additional pattern (Pattern E) which comprises non-conductive material only. Each package has a metallic foil lid that is truncated across its entire width. In fact the lid is truncated at each end in a symmetrical manner (e.g. as illustrated in FIG. 4a). This set of patterns is sufficient to encode 4 different package types, and it is envisaged that each package type can be associated with a different set of machine parameters. Each package type is encoded by a pair of patterns, with one pattern beneath coil 6a and the other pattern beneath coil 6b. A degree of redundancy is introduced into the coding system by grouping these pairs of patterns such that a given package type is encoded by multiple pattern pairs (see Table 1).

An advantage of this coding system is that it permits reliable package recognition even if the alignment of the edges of the conductive material with respect to the coils is somewhat variable. This is described more fully below.

TABLE 1

|  |  | Coil 6a | | | | |
| --- | --- | --- | --- | --- | --- | --- |
|  |  | Pattern A | Pattern B | Pattern C | Pattern D | Pattern E |
| Coil 6b | Pattern A | Type 1 | Type 1 | Type 2 | X | X |
|  | Pattern B | Type 1 | Type 2 | Type 2 | Type 3 | X |
|  | Pattern C | Type 2 | Type 2 | Type 3 | Type 3 | Type 4 |
|  | Pattern D | X | Type 3 | Type 3 | Type 4 | Type 4 |
|  | Pattern E | X | X | Type 4 | Type 4 | No foil |

Figure 5A:
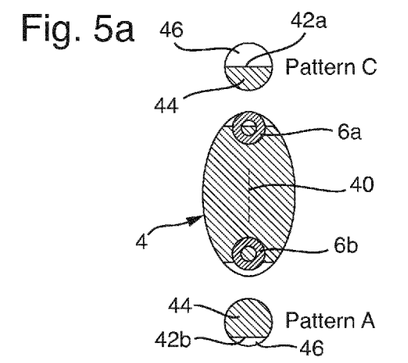
FIGS. 5a to 5e illustrate the effect of variation in package placement within the beverage production machine.
Figure 5B:
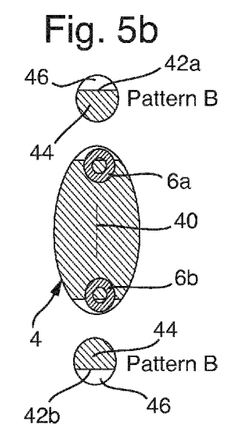
Figure 5C:
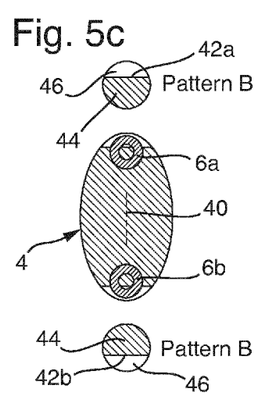

FIG. 5c shows a package which is aligned centrally with respect to the coils 6a, 6b. The pattern beneath each coil 6a, 6b corresponds to pattern B, therefore the package in FIG. 5c will be identified as package type 2.

Figure 5D:
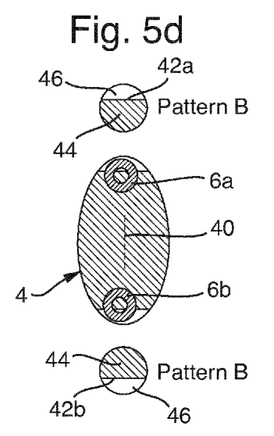

FIGS. 5b, 5c and 5d show the effect of varying the lateral placement of a package 4 within the beverage production machine. The package 4 of FIG. 5b has been shifted to the left, whilst the package 4 of FIG. 5d has been shifted to the right. Because the edge sections 42a, 42b are substantially straight, shifting the package laterally has no effect on the pattern beneath each coil 6a, 6b. Therefore the packages in FIGS. 5b and 5d will both be identified as package type 2. A similar result would be obtained if the variation were not in the placement of the package within the beverage production machine, but instead if the metallic foil lid were misplaced laterally with respect to the package.

Figure 5E:
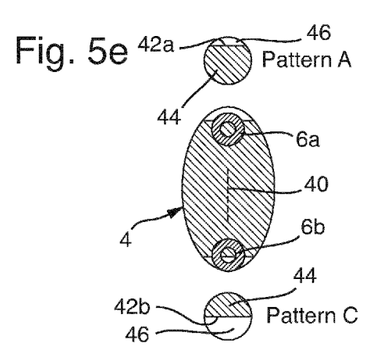

FIGS. 5a, 5c and 5e show the effect of varying the lengthwise placement of the package within the beverage production machine. The package of FIG. 5a has been shifted towards coil 6b, whilst the package of FIG. 5e has been shifted towards coil 6a. In this instance the patterns beneath each coil in FIGS. 5a and 5e are different from those shown in FIG. 5c: the foil beneath one coil corresponds to pattern A and the foil beneath the other coil corresponds to pattern C. However, due to the redundancy in the coding system, the packages in FIGS. 5a and 5e will still both be identified as package type 2. Again, a similar result would be obtained if the variation were not in the placement of the package within the beverage production machine, but instead if the metallic foil lid were misplaced lengthwise with respect to the package, i.e. if the foil lid was placed closer to one end of the package.

Figure 6A:
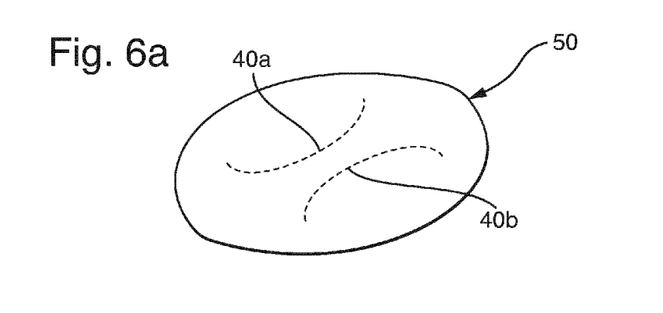
FIG. 6a is a perspective view of a package lid.
Figure 6B:
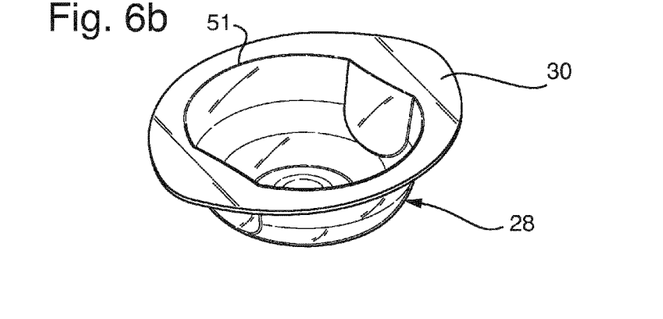
FIG. 6b is a perspective view of a package base unit.
Figure 6C:
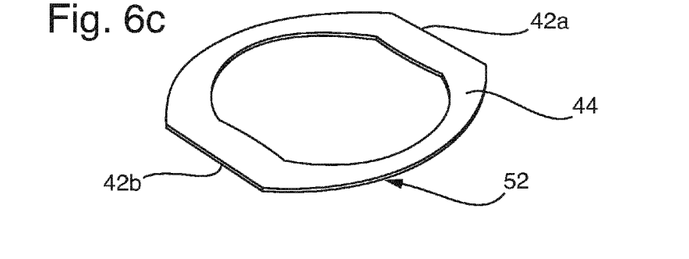
FIG. 6c is a perspective view of a package component consisting of a conductive material.

FIGS. 6a to 6c are perspective views of a lid, base unit and conductive component which can be assembled to form a package according to an embodiment of the present invention.

FIG. 6a shows a perspective view of a package lid 50. The lid is made from a non-conductive material, preferably a polymer film, and comprises two perforated lines 40a, 40b.

FIG. 6b is a perspective view of a base unit 28 with a rim 51. On assembly of the package, the lid is attached to the base unit around the rim 51, preferably by heat sealing. A projecting lip 30 extends wholly around the rim. The entire base unit is formed from a non-conductive material. This can be achieved, for example, by thermoforming a thermoplastic material such as polypropylene.

Figure 7:
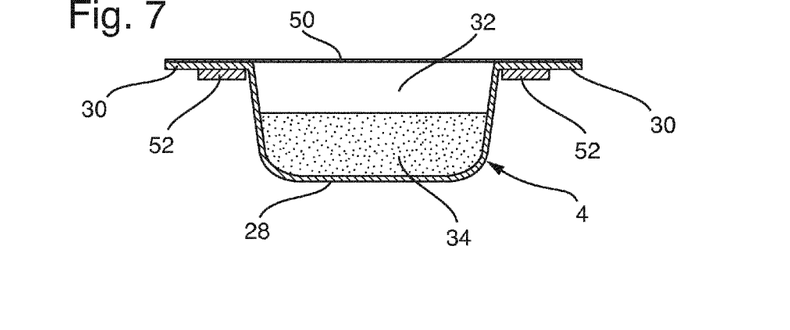
FIG. 7 shows a cross-sectional view of a package obtained by assembling the lid, base unit and component of FIGS. 6a to 6c.

FIG. 6c shows a perspective view of a component 52 consisting of a conductive material 44. Two edge section 42a, 42b traverse the conductive material 44 of the component 52. Once the component is associated with the base unit, these edge sections 42a, 42b become associated with the projecting lip 30. The component is preferably formed from aluminium. The component is shaped such that it can be associated with the base unit. Preferably, on assembly of the package the conductive material 44 of the component 52 is associated with the projecting lip such that it is situated beneath the lip (e.g. as shown in FIG. 7). However, it will be appreciated that the component 52 could equally well be placed on top of the lid, or between the base unit and the lid. The component can be physically attached to the base unit or lid (e.g. by gluing). However, it is also envisaged that the component is releasably associated with the projecting lip. For example, it will be appreciated that the component represented in FIG. 6c comprises a central opening which enables the component to releasably engage with the base unit of FIG. 6b.

Alternatively, the component 52 could rest on or be attached to the package holder, so that the projecting lip of the package rests on and becomes associated with the component 52 when the package is inserted into the package holder of the beverage production machine.

FIG. 7 shows a cross-sectional view of a package obtained by assembling the lid 50, base unit 28 and component 52 of FIGS. 6a to 6c. The base unit 28 defines a compartment 32 which encloses tea material 34. The lid 50 is attached to the base unit 28 around the rim. The component 52 is releasably associated with the underside of the projecting lip 30.

The invention claimed is:
1. A beverage production machine comprising:
a reservoir;
a chamber;
a pump;

a valve;

a heater; and an apparatus for recognising a package, the apparatus comprising:
- two resonant tank circuits, each one comprising a coil and a capacitor;
- two electronic detection circuits for detecting changes in coil impedance;
- a means for generating a signal, wherein the signal is indicative of the changes in coil impedance; and
- a control means communicable with the pump, the valve, and the heater, the control means for controlling at least one parameter of the beverage production machine according to the signal;

wherein the package comprises a base unit, the base unit having a first shape;

wherein the beverage production machine further comprises a package holder having a second shape, the package holder for selectively supporting the package within the machine and that interacts with the package to direct the location and alignment of the package within the beverage production machine such that the first shape aligns with the second shape in any one of n fixed orientations; and wherein n is an integer.

2. A beverage production machine as claimed in claim 1, wherein the control means controls one or more of the temperature, pressure, volume or flow rate of the brewing liquid, the path(s) the brewing liquid follows within the beverage production machine and/or the brewing time.

3. A beverage production machine as claimed in claim 1 which contains a package, the package comprising:
- a base unit having a compartment containing tea material, and a rim;
- conductive material associated with the package, the conductive material having two edge sections which are situated on opposite sides of the compartment; and
- a lid attached to the base unit around the rim so as to enclose the tea material within the package, the lid comprising:
  - a central lidding portion comprising at least one perforated line;
- wherein the package can be aligned within the beverage production machine in any one of n fixed orientations, wherein n is 1, 2, 3, or 4.

4. A package for a beverage production machine, the package comprising:
- a base unit having a compartment containing tea material and a rim;
- conductive material associated with the package, the conductive material having two edge sections which are situated on opposite sides of the compartment;
- a lid attached to the base unit around the rim so as to enclose the tea material within the package, the lid comprising:
  - a central lidding portion comprising at least one perforated line; and
  - a projecting lip extending partially or wholly around the rim;
- wherein the package can be aligned within the beverage production machine in any one of n fixed orientations;
- wherein n is 1, 2, 3, or 4;
- wherein the conductive material is associated with the projecting lip; and
- wherein the lid comprises a peripheral portion overlaying the projecting lip.

5. A package as claimed in claim 4, wherein the lid comprises the conductive material.

6. A package as claimed in claim 5, wherein the lid comprises metallic foil, preferably a laminate of aluminum foil and polyethylene.

7. A package as claimed in claim 4, wherein the projecting lip has an underside and the conductive material is associated with the underside of the projecting lip.

8. A package as claimed in claim 4, wherein the projecting lip comprises the conductive material.

9. A package as claimed in claim 4, wherein the edge sections are substantially straight-edged sections which are parallel to one another.

10. A package as claimed in claim 9, wherein the edge sections extend across the entire width of the projecting lip.

11. A package as claimed in claim 4, wherein the base unit is formed from a non-conductive material.

12. A package as claimed in claim 4, wherein the projecting lip is shaped so as to direct the alignment of the package within the beverage production machine.

13. A method of recognising a package as claimed in claim 4 in a beverage production machine according to claim 1, the method comprising:
- placing the package in the package holder;
- applying alternating current to the two coils while the package is stationary, the coils being positioned in the beverage production machine such that they generate eddy currents within the conductive material adjacent to the edge sections;
- detecting a change in coil impedance for each of the coils;
- generating a signal indicative of the change in impedance; and
- identifying the package according to the signal.

14. A method as claimed in claim 13, wherein the package is identified by comparing the signal to a number of reference signals, each one corresponding to a certain type of package; and
- wherein identification of the package controls at least one parameter of the beverage production machine.

15. A multipack containing a plurality of packages according to claim 4.

16. A package for a beverage production machine, the package comprising:
- a base unit having a compartment containing tea material and a rim;
- a projecting lip;
- conductive material associated with the projecting lip, the conductive material having two edge sections which are situated on opposite sides of the compartment; and
- a lid attached to the base unit around the rim so as to enclose the tea material within the package, the lid comprising:
  - a central lidding portion comprising at least one perforated line;
- wherein the package can be aligned within the beverage production machine in any one of n fixed orientations;
- wherein n is 1, 2, 3, or 4;
- wherein the base unit is formed from a non-conductive material; and
- wherein the projecting lip is shaped so as to direct the alignment of the package within the beverage production machine.

17. A package as claimed in claim 16, wherein the projecting lip extends partially or wholly around the rim.

* * * * *